United States Patent [19]

Saito et al.

[11] Patent Number: 5,120,506

[45] Date of Patent: * Jun. 9, 1992

[54] CHEMICAL ANALYZER

[75] Inventors: Yoshio Saito, Saitama; Shinichi Matsuda, Kanagawa; Keishiro Kido; Kimiko Ishizuka, both of Saitama, all of Japan

[73] Assignee: Fuji Photo Film Co., Ltd., Kanagawa, Japan

[*] Notice: The portion of the term of this patent subsequent to Oct. 2, 2007 has been disclaimed.

[21] Appl. No.: 448,443

[22] Filed: Dec. 11, 1989

[30] Foreign Application Priority Data

Dec. 16, 1988 [JP] Japan .................. 63-318064

[51] Int. Cl.⁵ .................................................. G01N 31/00
[52] U.S. Cl. .................................. 422/66; 422/67; 436/44; 436/46; 436/170; 34/153
[58] Field of Search .................................. 422/63–67; 436/43, 44, 46, 170; 34/153, 155

[56] References Cited

U.S. PATENT DOCUMENTS

| | | | |
|---|---|---|---|
| 3,260,413 | 7/1966 | Natelson | 222/144 |
| 3,526,480 | 9/1970 | Findl et al. | 422/66 |
| 3,728,081 | 4/1973 | Bidauset | 422/66 |
| 3,992,158 | 11/1976 | Przybylowicz et al. | 422/66 |
| 4,089,747 | 5/1978 | Bruschi | 195/99 |
| 4,292,272 | 9/1981 | Kitajima et al. | 422/56 |
| 4,558,946 | 12/1985 | Galle et al. | 422/63 |
| 4,708,886 | 11/1987 | Nelson | 422/64 |
| 4,782,018 | 11/1988 | Gikeuberry et al. | 436/170 |
| 4,783,315 | 11/1988 | Arai et al. | 422/56 |
| 4,861,552 | 8/1989 | Masuda et al. | 422/56 |
| 4,876,204 | 10/1989 | Inoue et al. | 422/63 |
| 4,908,320 | 3/1990 | Zakowski et al. | 422/64 |
| 4,954,319 | 9/1990 | Koizumi et al. | 422/64 |
| 4,959,976 | 10/1990 | Matsuda et al. | 422/66 |

FOREIGN PATENT DOCUMENTS

| | | |
|---|---|---|
| 0122641 | 10/1984 | European Pat. Off. . |
| 0162301 | 11/1985 | European Pat. Off. . |
| 0162302 | 11/1985 | European Pat. Off. . |
| 2792 | 1/1977 | Japan .................. 436/44 |

Primary Examiner—Lynn M. Kummert
Attorney, Agent, or Firm—Sughrue, Mion, Zinn Macpeak & Seas

[57] ABSTRACT

A chemical analyzer has a cold-storage chamber and a tape-feeding cassette which can be accommodated in the cold-storage chamber and is detachable therefrom. The cassette contains a chemical analysis tape and has an opening through which the tape can be taken out of the cassette. A section of the tape-feeding cassette inside of the opening is sealed off from the atmosphere and from other parts of the cassette. The tape passes through this section. This section is provided with air which has a relative humidity not higher than 70% such that the pressure therein is positive.

6 Claims, 4 Drawing Sheets

CHEMICAL ANALYZER

BACKGROUND OF THE INVENTION

1. Field of the Invention

The present invention relates to a chemical analyzer in which chemical analysis films, especially tape-like films (chemical analysis tape), are used to determine the amount of specific components contained in liquid samples, especially biological body fluids such as blood, serum, and urine; and, in particular, to a chemical analyzer which is characterized in the special structure of a tape-feeding cassette for accommodating the tape-like film.

2. Description of the Prior Art

The determination of the amount of various metabolites, e.g. glucose, bilirubin, urea-nitrogen, uric acid, cholesterol, lactate dehydrogenase, creatine kinase, GOT(AST), and GPT(ALT), in body fluids is important in the field of clinical medicine and is essential to the diagnosis of diseases, follow-up studies of medical treatments, judgments on prognosis, etc. In clinical chemical analyses in which blood or the like is used as liquid samples, it is preferable if a highly accurate analysis can be conducted with a very small amount of the liquid sample. Conventionally, wet-type methods which employ reagents solution have been widely used. However, these methods cannot be conducted quickly.

As an analysis means for quickly conducting a highly accurate analysis with a very small amount of a liquid sample, chemical analysis slides in which dry-type multilayer films (film-shaped multi-layer analysis elements) are used have been developed and are disclosed in U.S. Pat. Nos. 3,992,158 and 4,292,272, for example. In a chemical analysis slide, each dry-type multilayer chemical analysis film, in which a support, a reagent layer, a light reflection layer, and a liquid spreading layer are superposed in this order, for example, is accommodated in a mount. One slide is used for one analyte (i.e., one specific component to be analysed) of a liquid sample.

When a long chemical analysis film tape is used instead of such a slide, the time and expense required to provide a slide accommodating a film chip for each unit of analysis can be omitted. Chemical analysis tapes are disclosed, in combination with analyzers, in U.S. Pat. Nos. 3,260,413 and 3,526,480, and the like. Also, U.S. Pat. No. 3,992,158 mentions such a chemical analysis tape. However, as noted in U.S. Pat. No. 3,992,158, in most of those disclosed in U.S. Pat. Nos. 3,260,413 and 3,526,480, at least two tapes are brought into contact with each other so that a complex structure is temporarily formed, and thereafter the tapes are separated from each other. Accordingly, the structure of the analyzer becomes complicated. U.S. Pat. No. 3,992,158 mentions that the analysis tape described therein is advantageous in that it does not require a complicated apparatus and in that various kinds of tapes can be used simultaneously or successively.

In cases where an analysis slide is used for each sample fluid, it is only necessary for the desired number of slides to be taken out of a container or a storage chamber immediately before their use or on the day they are to be used. On the other hand, an analysis tape has to be installed as a whole in an analyzer. Accordingly, when an analysis slide would become unstable during the time it is stored after it has been unpacked and a rolled analysis tape is used instead of a slide, it is necessary that the rolled analysis tape as a whole be accommodated in a cold-storage chamber which keeps the tape at a temperature within the range of 1° C. to 18° C. A chemical analyzer may have such a cold-storage chamber.

In a chemical analyzer which has a cold-storage chamber for accommodating an analysis tape, since the temperature of the tape at the outlet of the cold-storage chamber is low, the atmospheric moisture is likely to form dew on the tape. In this case, the moisture content of the analysis tape increases and the performance thereof will deteriorate. In order for this problem to be overcome, it may be preferable for a low-moisture airflow to be provided near the outlet of the cold-storage chamber. However, even when a low-moisture airflow is provided at the surface of an analysis tape which is taken out of the cold-storage chamber, the deterioration of the analysis tape due to the increase in the moisture content cannot sufficiently be eliminated.

Also, when the tape outlet of the cold-storage chamber is not sealed, the atmosphere may invade the cold chamber and dew may form on the part of the tape near the outlet. It may be desirable for a means for sealing the tape outlet of the cold-storage chamber to be provided at least during the time when the tape is not being conveyed. However, even when a means for sealing the tape outlet of the cold-storage chamber is provided, it is practically impossible to eliminate the deterioration of the analysis tape due to the increase in the moisture content.

SUMMARY OF THE INVENTION

The object of the present invention is to provide a chemical analyzer having a cold-storage chamber and accommodating a chemical analysis tape, in which analyzer the deterioration of the performance of the analysis tape due to an increase in the moisture near the outlet of the cold-storage chamber is sufficiently eliminated.

The present invention provides a chemical analyzer having a cold-storage chamber and a tape-feeding cassette which can detachably be accommodated in said cold-storage chamber, said cassette containing a chemical analysis tape and having an opening through which said chemical analysis tape can be taken out of said cassette;

said cold storage chamber accommodating said cassette such that said cassette is detachable therefrom and said opening faces the outside of said cold-storage chamber;

said opening having a first sealing means for preventing air from entering but permitting said tape to pass therethrough;

said cassette having a section inside of said opening, through which section said tape passes, and a second sealing means for preventing air from entering but permitting said tape to pass therethrough, said second sealing means being disposed between said section and other parts of said cassette; and said section being provided with air which has a relative humidity not higher than 70% such that the pressure in said section be positive with respect to the exterior air pressure.

The object of the present invention is achieved by the above analyzer.

The chemical analyzer in accordance with the present invention has a cold-storage chamber and a tape-feeding cassette, which cold-storage chamber accommodates the tape-feeding cassette such that it can be detached therefrom.

The tape-feeding cassette accommodates the chemical analysis tape and has an opening through which said chemical analysis tape can be taken out. The cassette has a structure such that it can be detachably accommodated in the cold-storage chamber. Only the opening in the cassette faces the outside of the cold-storage chamber; the other parts are accommodated in the cold-storage chamber. Although the tape is generally wound around a spool and accommodated in the cassette as a roll, the spool may be omitted. The tape can also be accommodated in the cassete such that it is skewed or zigzag with respect to the direction of travel of the tape through the analyzer. The cassette is formed of a moisture-impenetrable material, e.g. synthetic polymer such as polystyrene, and is tightly closed off from the exterior such that the air can enter only through the opening therein.

Preferably, the cold-storage chamber can maintain a temperature within the range of not lower than 1° C. and not higher than 18° C. therein.

The opening through which the tape is taken out of the cassette has a sealing means which prevents air from entering said cassette but permits said tape to pass therethrough. This sealing means comprises, for example, a pair of thin rubber sheets (any of natural and synthetic rubbers, e.g. silicone rubber), a pair of sponges (foam rubber), and the like which are vertically disposed such that the tape is held therebetween. Preferably, a space having a width corresponding to the width of the tape is provided in the sealing means so that the tape can pass therethrough, while the other parts of the cassette are tightly closed.

A small section is provided inside of the opening in the cassette. This section is separated from the other parts of the cassette by a second sealing means which prevents air from entering said cassette but permits said tape to pass therethrough. This sealing means may be the same as that provided at the opening through which tape is taken out of said cassette. The length of this small section, which lies in the direction in which said tape travels, may suitably be 3 to 30 mm when the width of the tape is 3 to 10 mm. It is unnecessary to make this section too long. In general, it is preferable that the width of this section be the same as that of the portion of the cassette which accommodates said tape. Accordingly, in general, the width of this section is slightly larger than that of the tape, for example, by 1 to 8 mm.

This section is provided with air having a relative humidity not higher than 70% such that the pressure in the section be positive with respect to atmospheric pressure. It is sufficient for this section to have a pressure higher than that of the atmosphere by 4 mmHg to 60 mmHg. Preferably, the relative humidity is not higher than 50%.

In the cassette used in the present invention, an airflow with a low humidity is circulated within the above-mentioned section disposed near the opening in the cassette, and thereby the atmosphere is prevented from flowing into the tape-accommodating portion of the cassette. Preferably, the moisture content of the airflow is such that the relative humidity is not higher than 70% at the temperature of the cold-storage chamber which accommodates the cassette. Most preferably, the temperature of the airflow is substantially the same (e.g. ±2° C.) as that in the cold-storage chamber. However, the temperature of the airflow may be the same as that of the atmosphere, or a temperature therebetween. Although the temperature of the airflow may be lower than the temperature in the cold-storage chamber, if it were, the means for lowering the relative humidity of the airflow itself would be large and costly. An airflow temperature higher than that of the atmosphere is undesirable since it greatly influences the temperature in the cold-storage chamber. However, the former can be slightly higher than the latter (e.g. by 3° C.).

Since the airflow introduced into the above-mentioned section has a slightly positive pressure, most of the air flows out of the section, while a part thereof flows into the cassette. Since the air flowing into the cassette has a low humidity, no dew is formed on the tape and the moisture content of the tape is not unfavorably increased. Also, since the atmosphere is prevented from invading the cassette, the moisture in the atmosphere does not influence the tape.

Means for providing a low-humidity airflow to the above-mentioned section comprises, for example, a low-humidity air generator which takes in air, removes the moisture therein, and then sends out air having a low humidity, and a duct which introduces the low-humidity air from the generator to the above-mentioned section. The front end of this duct opens into the lower surface, side surface, or upper surface of the above-mentioned section in the cassette. Preferably, it opens into the lower surface or the side surface of the above-mentioned section. Most preferably, it opens into the lower surface of the above-mentioned section. The amount of air delivered to said section must be sufficient for maintaining a positive pressure therein. To maintain a sufficient airflow, the cross-sectional area of the duct has an inner diameter in the range of 1 to 7 mm of a circular form. Preferably, the heat is kept in the duct. In order to prevent the temperature from changing, the duct should not be too long. The duct may be located on the exterior, the interior, or within the walls of the cold-storage chamber. Advantageously, the duct is located within a wall of the cold-storage chamber in order to prevent the temperature of the airflow from changing. That is, most preferably, the duct passes through a wall of the cold-storage chamber and is connected to the lower surface of the above-mentioned section within the cassette.

As the analysis tape in the analyzer of the present invention, the one disclosed in U.S. Pat. Nos. 4,292,272 and 4,861,552, and EP-A-0162302, for example, is preferably used.

When a water-impermeable and light transmissive support is used, the analysis tape used in the present invention, for example, may have the following layer structures:

(1) a structure in which a liquid-spreading layer containing a reagent composition is disposed on a support;
(2) a structure in which a support, a reagent layer, and a liquid-spreading layer are superposed in this order;
(3) a structure in which a support, a detection layer, a reagent layer, and a liquid-spreading layer are superposed in this order;
(4) a structure in which a support, a reagent layer, a light-reflection layer, and a liquid-spreading layer are superposed in this order;
(5) a structure in which a support, a detection layer, a reagent layer, a light-reflection layer, and a liquid-spreading layer are superposed in this order; and
(6) a structure in which a support, a detection layer, a light-reflection layer, a reagent layer, and a liquid-spreading layer are superposed in this order.

In the above structures (1), (2) and (4), a water-absorptive layer may be disposed between the support and the liquid-spreading layer or the reagent layer. In the above structures (2), (3), and (4), a blood cell-filtering layer may be disposed between the reagent layer and the detection layer or the liquid-spreading layer. Further, in the above structures (4), (5), and (6), a blood cell-filtering layer, an interferents-removing layer, or the like may be disposed between the light reflection layer and the detection layer, the reagent layer, or the liquid-spreading layer, between the reagent layer and the detection layer, or between the reagent layer and the liquid-spreading layer. Generally, the detection layer is a layer into which a dye or the like, which is generated in the presence of the analyte, is diffused and can optically be detected through the light-transmissive support. The detection layer may be formed of a hydrophilic polymer. Generally, the water-absorptive layer is a layer into which the dye, which is generated in the presence of the analyte, is not substantially diffused. The water-absorptive layer may be formed of an easily-swelling hydrophilic polymer.

Preferably, when the liquid sample is supplied to the liquid-spreading layer, it distributes a uniform amount per unit area to the adjacent water-permeable layer. A useful liquid-spreading layer comprises a fibrous material such as the woven fabrics (woven cloths) disclosed in U.S. Pat. No. 4,292,272 or the knitted fabrics (knitted cloths) disclosed in EP-A-0162302. The fabric or the like may be subjected to a glow-discharge treatment as disclosed in U.S. Pat. No. 4,783,315. In order to control the spreading area, the spreading speed, and the like, the liquid-spreading layer may contain a hydrophilic polymer or a surfactant such as the one disclosed in EP-A-0162301.

An adhesive layer for bonding and laminating the liquid-spreading layer may be disposed on such a layer as the reagent layer, the light-reflection layer, the filtering layer, the water-absorptive layer, or the detection layer. Generally, the adhesive layer comprises a hydrophilic polymer, e.g. gelatin, gelatin derivative, polyacrylamide, or starch, which can bond a porous layer when being swelled by water.

The analysis tape used in the present invention may have a light-reflection layer (between the reagent layer and the detection layer or between the reagent layer and the liquid-spreading layer, for example). When the detectable change (coloring, change of a color, or the like) is measured from the side of the light-transmissive support, which is possible because of the reflective natures of the light-reflection layer, the light-reflection layer shields the color of the liquid sample supplied to the liquid-spreading layer, while functioning as a light-reflection layer or a background layer. In particular, when the sample is whole blood, the light-reflection layer shields the red color of hemoglobin, the yellow color of bilirubin, or the like. Preferably, the light-reflection layer comprises a water-permeable layer in which light-reflective particulates such as those of titanium oxide, barium sulfate, or the like are dispersed in a binder of a hydrophilic polymer.

The reagent layer or the like in the analysis tape used in the present invention contains a composition which can generate an optically-detectable material such as a dye. For example, compositions which can generate a dye upon oxidation of a leuco dye (e.g. triarylimidazole leuco dye disclosed in U.S. Pat. No. 4,089,747, diarylimidazole leuco dyes disclosed in EP-A-0122641 or the like), compositions containing a compound which is coupled with another compound and forms a dye when oxidized (e.g. 4-aminoantipyrins with phenols or naphthols), or compositions comprising a compound which can generate a dye in the presence of a reduction-type coenzyme and an electron carrier can be used. Also, in cases where the analysis tape is used for measuring an enzymatic activity, a self-coloring substrate which can isolate a colored material such as p-nitrophenol may be included in the reagent layer, the liquid spreading layer, or the like. In addition to a substantially uniform reagent layer containing a hydrophilic polymer as a binder, a porous material may be used as the reagent layer.

Preferably, the diameter of the roll of the analysis tape is not smaller than 30 mm. In cases where the thickness of the analysis tape is not smaller than 0.50 mm or where the tape has a nonfibrous porous layer, it is preferable for the diameter of the roll of the tape to be not smaller than 40 mm. In general, the analyzer has a section at which a liquid sample can be applied to the tape, and the temperature of the tape disposed between the outlet of the cold-storage chamber and the sample applying section approximates room temperature before it is used for an analysis. The length of the tape in this portion is preferably not greater than 80 mm and more preferably not greater than 50 mm.

In order to reduce the number of sample-applying means used for a plurality of analysis tapes, a dispenser, which dispenses the liquid sample, may linearly be moved between at least two sample-applying positions.

Also, in order to use many kinds of analysis tapes simultaneously or successively, it is necessary that a plurality of probes for optically measuring color density or the like be provided for each analysis tape or that a single optical probe or a few optical probes be used commonly for all the tapes (or for all the groups of tapes). In order to reduce the number of light sources used for optical measurement or to eliminate the necessity for moving them, a single light source for optical measurement may be provided for two or more measuring points, and a light-guiding member such as an optical fiber may be used to guide the illuminating light to the measuring points for each tape such that the optical density of the tape is measured via reflection. In order to eliminate the necessity of moving the necessary optical measurement systems, the light reflected from an analysis tape at each measuring point is guided to the corresponding light-measuring element via an individual light-guiding member such as an optical fiber. Then the amount of the reflected light is measured. Preferably, in this case, a desired spectral filter is disposed between the outlet end of the optical fiber and the light-measuring element. If the spectral filter is disposed on the light source side, it should be exchangeable.

In order to reduce the size of the analyzer, it is preferable for the sample-applying operation, the incubation, and the optical measurement to be conducted without moving the tape. A tape-preheating means may be provided such that the tape is heated before entering into the sample-applying section.

DESCRIPTION OF THE PREFERRED EMBODIMENTS

In the following, an embodiment of the present invention is described with reference to the attached drawings.

Figure 1:
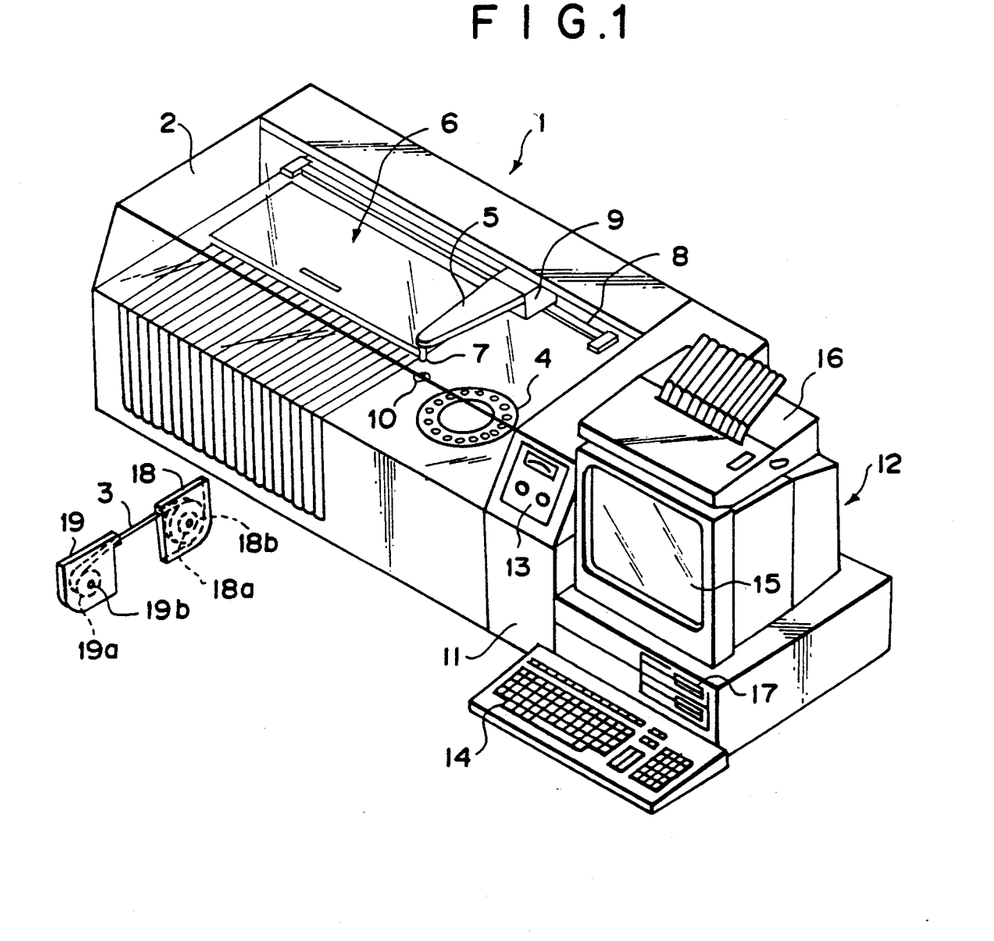
FIG. 1 is a perspective view showing the chemical analyzer in accordance with the present invention.

FIG. 1 is a perspective view showing the chemical analyzer in accordance with the present invention. The chemical analyzer has a built-in cold-storage chamber.

The chemical analyzer 1 shown in this drawing has a transparent cover 2. The cover 2 is opened when a liquid sample, a tape-feeding cassette, and the like, which will be described hereinbelow, are introduced into the analyzer 1 or taken out therefrom. The analyzer 1 has a sample-containing means 4 which contains a circularly-arranged liquid sample such as blood serum or urine. As will be described later, the liquid sample contained therein is taken out therefrom by a sample-applying means 5, such as a pipette, and is applied to a plurality of analysis tapes 3. Each analysis tape 3 contains a specific reagent which reacts with a corresponding chemical component (a solid component, occasionally) in the liquid sample, and exhibits a color due to the reaction. Each analysis tape 3, which is rolled up by a tape-feeding cassette 18 and a tape wind-up cassette 19, is received in the analyzer 1. The unused portion of the analysis tape 3 is rolled up within the tape-feeding cassette 18, while a winding leader portion and the portion which has already been used for making measurements are rolled up within the tape wind-up cassette 19. In the center portion of a reel 19a within the cassette 19, a hole 19b which engages a rotary shaft of a motor is provided. In the center portion of a reel 18a within the cassette 18, a hole 18b which contains a desiccating agent (e.g. zeolite, silica gel) is provided. In the analyzer 1, a plurality of tape-feeding cassettes can be received in parallel in a tape-accommodating means 6, which allows a plurality of items (components to be analyzed, i.e., analytes) to be measured simultaneously.

The sample-applying means 5 has a sample-applying nozzle 7 at its tip and is moved by a movable supporting member 9, which is mounted on a rail 8, in a direction parallel to the rail 8 such that the liquid sample can be taken out of the sample-containing means 4 and then applied to the analysis tape 3, which has been drawn out of the tape-accommodating means 6. The sample-applying means 5 can also be moved vertically. The sample-applying means 5 is in a raised position when it moves along the rail 8, and it is lowered while a sample is being taken out and applied to the tape and while it is being washed as will be described later.

After the liquid sample is applied to the analysis tape, the sample-applying nozzle 7 is washed at a nozzle-washing station 10, which is disposed between the tape-accommodating means 6 and the sample-containing means 4, and then is reused for applying the next liquid sample. The analysis tape to which the liquid sample has been applied is incubated (heated) by an incubator as will be described later, and then the coloring, change in color, or the like is measured by an optical measurement means.

The analyzer 1 is controlled by a circuit section 11 and a computer 12, which are connected to the analyzer 1 and which also process the measured data. An operation and display section 13 disposed in the front surface of the circuit section 11 has a power switch, an ammeter for monitoring the electric current consumed in the analyzer 1, and the like. The computer 12 has a keyboard 14 at which instructions are input into the analyzer 1; a CRT display 15 which displays auxiliary information concerning the instructions, the results of a measurement, or the like; a printer 16 which prints out the results of a measurement; and a floppy disk drive 17 which stores commands for controlling the analyzer 1, the data gained from the measurement, and the like.

Figure 2:
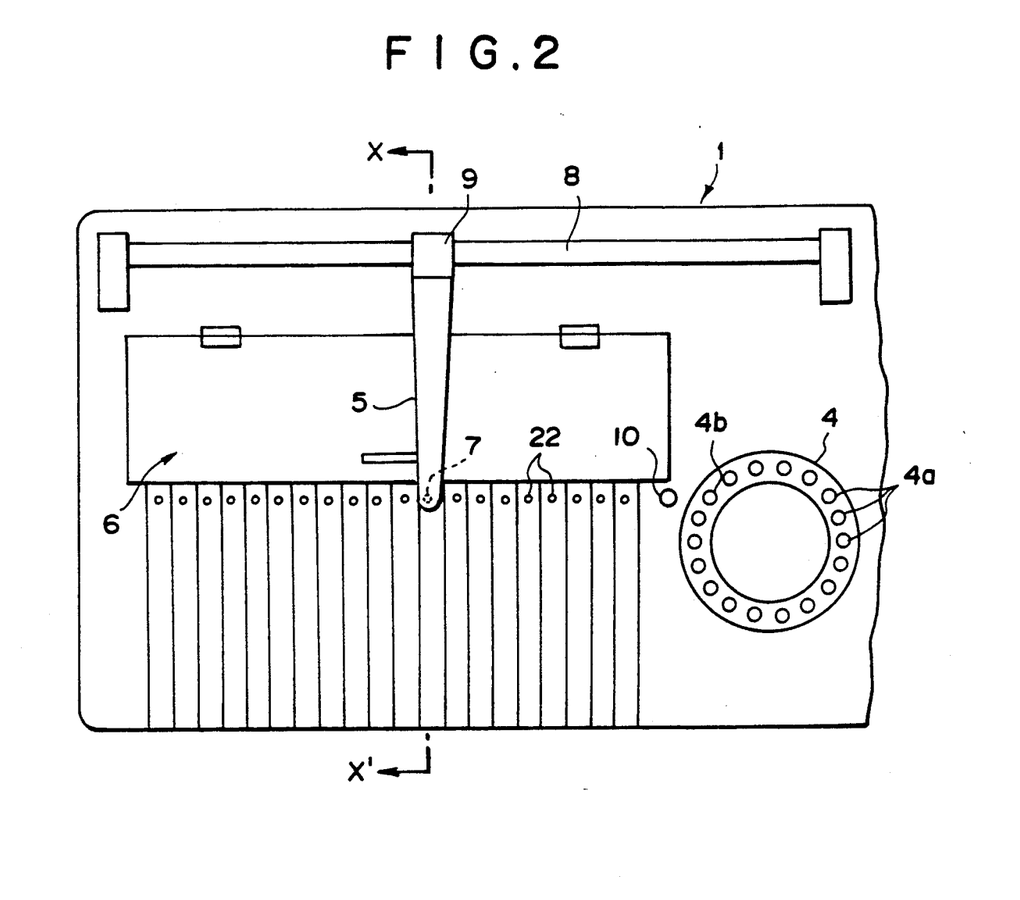
FIG. 2 is a plan view showing the main part of the chemical analyzer shown in FIG. 1.

FIG. 2 is a plan view showing the main part of the chemical analyzer shown in FIG. 1.

The tape-accommodating means 6 is constructed such that sample-applying positions 22 on the analysis tape, which is drawn out of the tape-feeding cassettes accommodated therein, are arranged in a line. Also, the nozzle washing portion 10 and a sample-drawing position 4b of the sample-containing means 4 are arranged along this line.

In the sample-containing means 4, a plurality of vessels for holding liquid samples are circularly contained in a container portion 4a. The container portion 4a is rotated by a rotating means (not shown) such that the liquid sample for the next measurement is positioned at the sample-drawing position 4b. The sample-applying means 5 is moved by the movable supporting member 9, which is mounted on the rail 8, in the direction in which the rail 8 extends. Under the control of the computer 12, the sample-applying means 5 draws in the liquid sample from the container located at the sample-drawing position 4b, and then applies it to the desired analysis tape 3 at the sample-applying position 22.

Figure 3:
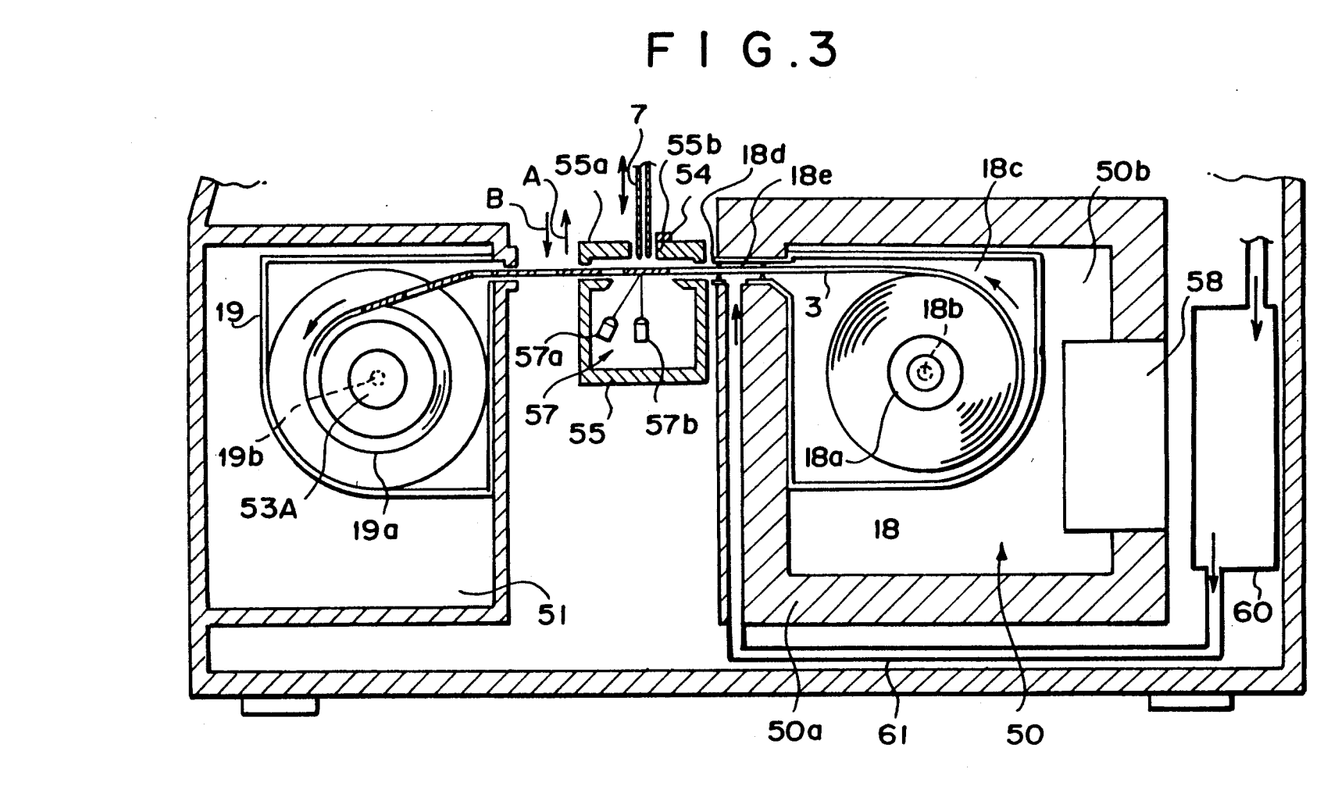
FIG. 3 is a schematic view showing the main part of the cross section taken along line X-X' of FIG. 2.

FIG. 3 is a schematic view showing the main part of a cross section taken along line X-X' of FIG. 2. Initially, the main portion of the analysis tape 3 is contained in the tape-feeding cassette 18 and is accommodated in the analyzer 1. As the analysis tape 3 is used for measurements, it is successively taken up by the tape wind-up cassette 19. The tape-feeding cassette 18 is accommodated in a cold-storage chamber 50, the inside of which is kept at 15° C., for example, while the tape wind-up cassette 19 is accommodated in a winding-up chamber 51. In the cold-storage chamber 50, the tape-feeding cassette 18 is accommodated in a cassette-accommodating portion 50b, which is enclosed by walls 50a formed of a heat-insulating material. The walls 50a are provided with a cooling apparatus 58, which generates a cold airflow depending on the temperature in the chamber. The temperature in the chamber is detected by a temperature sensor, and the cassette-accommodating portion 50b is cooled to a predetermined low temperature. The shape of the cassette-accommodating portion 50b allows the cold airflow to be circulated and kept at a substantially uniform temperature. Accordingly, the temperature in the tape-feeding cassette 18 in the cassette-accommodating portion 50b is maintained at the above-mentioned low temperature. The cassette 18 is made of polystyrene, and is tightly enclosed such that the air cannot enter thereinto except at an opening 18d through which the tape can be taken out. The analysis tape 3 in the cassette 18 is drawn out of the cassette 18 through the opening 18d and is wound up by the tape wind-up cassette 19 after passing through an incubator 55.

In the center portion of the reel 19a within the cassette 19, a hole 19b is provided. This hole engages a rotary shaft of a wind-up motor 53A. As the motor 53A rotates, the analysis tape 3 is rolled around the reel 19a. In this way, the analysis tape 3, which has been drawn out of the tape-feeding cassette 18, is taken up by the tape wind-up cassette 19.

The incubator 55 is disposed at a position between the tape-feeding cassette 18 and the tape wind-up cassette 19, where the analysis tape 3 is held. The analysis tape 3 is held within the incubator 55 and successively passes therethrough. An optical measurement means 57, which measures the optical density of a coloring reaction or the like (change of a color or fluorescence) generated by a specific ingredient in the liquids on the analysis tape, is disposed within the incubator 55.

As the motor 53A rotates, the analysis tape 3 is intermittently drawn from the tape-feeding cassette 18 and intermittently conveyed in the leftward direction in the drawing. When the tape 3 is being conveyed, an upper lid 55a is raised in the direction of arrow A. When the tape 3 is no longer being conveyed, the upper lid 55a is moved down in the direction of arrow B and presses down the tape 3. Then a shutter 54 moves in the rightward direction in the drawing and opens a nozzle-inserting opening 55b. As shown in the drawing, the nozzle 7 moves down through the nozzle-inserting opening 55b and applies the liquid sample to the analysis tape 3. Thereafter the shutter 54 moves in the leftward direction and closes the nozzle-inserting opening 55b, and thereby the inside of the incubator 55 is maintained at a predetermined temperature (e.g. 37° C.). The portion of the tape 3 where the liquid sample is applied and spread (indicated by oblique lines in FIG. 3) is held at a constant temperature for a predetermined time (e.g. 4 minutes) in the incubator 55. After or during the incubation, the optical measurement means 57 measures the optical density of the portion of the analysis tape where the liquid sample has been applied. Light containing a preselected wavelength is emitted from a light source 57a such that the lower surface of the tape 3 is illuminated. The light reflected by the tape 3 is detected by a photodetector 57b, and thereby the optical density is measured.

After the sample-application, incubation, and measurement have been completed for one of the liquid samples, and a new portion of the analysis tape 3 has been drawn out of the tape-feeding cassette 18, the next liquid sample can be applied to the tape 3. After the completion of a measurement on a liquid sample, the analysis tape 3 is not moved until the new portion thereof, which to be used for the next measurement, is conveyed to the sample-applying position, which happens immediately before the next application of a sample.

Figure 4:
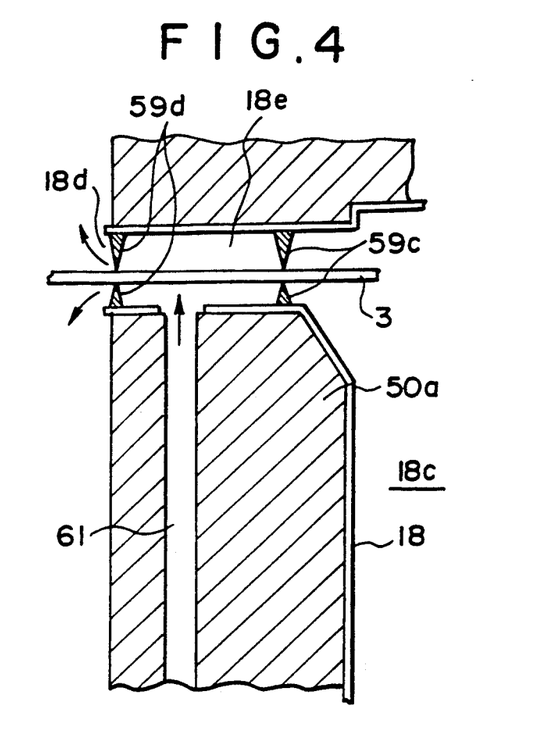
FIG. 4 is an enlarged cross-sectional view showing the main parts of the cold-storage chamber and the cassette.
Figure 5:
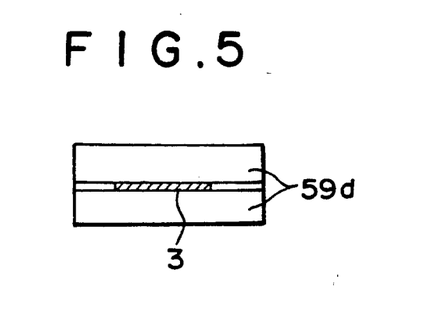
FIG. 5 is a schematic view showing the air-blocking curtains and the cross section of the analysis tape.

Adjacent to the opening 18d, through which the tape is taken out of the cassette, the tape-feeding cassette 18 has a small section 18e through which the tape 3 can pass. A low-humidity airflow is supplied to this section so as to prevent the atmosphere, which has a relatively high humidity, from invading the tape-feeding cassette 18. As shown in FIG. 4, air-blocking curtains 59c and 59d formed of silicone rubber or the like are respectively disposed between the section 18e and a tape-accommodating space 18c in the cassette 18 and at the opening 18d such that the section 18e is formed therebetween. The analysis tape 3 is drawn out of the cassette 18 through slits formed in the curtains 59c and 59d.

Means for supplying the above-mentioned airflow comprises a low-humidity air generating apparatus 60 which converts the atmosphere into low-humidity air (e.g. humidity of about 10%) and sends it out, and a duct 61 which guides the low-humidity air to the section 18e. Although some of the low-humidity air supplied to section 18e flows into the cassette 18 through the slit in the curtain 59c, most of it flows out of the cassette 18 through the slit in the curtain 59d. In this embodiment, it was evidenced that the analysis tape in the cassette could be maintained in a desirably dry condition even when the atmosphere had a temperature in the range of 35° C. to 40° C. and a relative humidity of 80 to 90%.

The above embodiment may be modified such that the slit in the curtain 59d is larger than about 1 mm, thus causing most of the low-humidity air to flow out of the cassette 18 through the slit in the curtain 59d.

As in the case of the first embodiment, it was evidenced that the analysis tape in the cassette could be maintained in a desirably dry condition even when the atmosphere had a temperature in the range of 35° C. to 40° C. and a relative humidity of 80 to 90%.

EXPERIMENT

An analysis tape having a width of 5 mm and a length of 5 m was used for measuring whole bilirubin and was wound around a reel having a diameter of 50 mm in a polystyrene cassette (having an inner volume of about 88 ml). The cassette had a cross section as shown in FIG. 4. In the outlet portion, 0.5 mm-thick silicone rubber sheets (having a hardness of 45±5°) were disposed at two points which were separated by 18 mm such that a small section (having a volume of about 0.53 ml) was formed therebetween. In each silicone rubber sheet, a slit having a length identical to the width of the tape was formed at a position where the sheet could be divided into two equal parts. The analysis tape was drawn out of the cassette through the slit. Both ends of the slit were further cut in a normal direction for about 1 mm such that the analysis tape could easily pass through the slit, while the airflow was blocked. A paper bag containing 1.3 g of zeolite desiccating agent (Zeolam A4 manufactured by Toso Co., Ltd.) was disposed in the center portion of the cassette, while a paper bag containing 0.5 g of the same was disposed at a position inside the cassette near the above-mentioned section.

Immediately after the winding-up of the tape, the cassette was accommodated in the cold-storage chamber of the analyzer whose cross section is shown in FIG. 3, which chamber was held at 15° C., and air having a relative humidity of 10% (a vapor pressure of 1.28 mmHg) was supplied to the above-mentioned section at a rate of 0.6 ml/sec.

With an external temperature of 32° C. and an external relative humidity of 80%, the change in the whole bilirubin content was measured in an analysis tape before and after five days of storage in a case where the above-mentioned airflow was supplied to the small section of the cassette (the present invention) and compared with that in a case where the airflow was not supplied (control). The analyzer shown in FIG. 3 was used for the measurement. Namely, the analysis tape 3 was drawn out of the cassette 18, a standard liquid was applied to the tape 3 at the incubator 55, the tape 3 was incubated, and then, from the lower surface of the tape 3, the optical measurement means 57 measured the optical density of the portion of the analysis tape where the standard liquid had been applied. As the standard liquid, a liquid having a whole bilirubin content of 0.4 mg/dl was used. The bilirubin (BIL) content was determined with reference to a standard curve. A new analysis tape was used to form the standard curve.

The measurement was conducted immediately after the tape was accommodated in the cassette and five days after the cassette was stored in the cold-storage chamber. The measurement after the tape had been stored for five days was conducted for a portion (1) of the tape (having a length of 18 mm) which had been present within the small section 18e and a portion (2) thereof having a length of 18 mm which extended from the portion (1) to the inside of the cassette. The results of the measurement are shown in Table 1. In the table, numerals refer to BIL content (mg/dl).

TABLE 1

| | INITIAL | AFTER FIVE DAYS IN STORAGE | |
|---|---|---|---|
| | | PORTION (1) | PORTION (2) |
| WITH AIRFLOW (PRESENT INVENTION) | 0.4 | 0.4 | 0.4 |
| WITHOUT AIRFLOW (CONTROL) | 0.4 | 1.2 | 0.6 |

As is clear from the table, the apparent BIL content increased due to the deterioration of the analysis tape in both of the portions (1) and (2) in the case where an airflow was not supplied (where the tape-accommodating portion and the atmosphere were merely divided from each other by the small section), while the BIL content did not change and the analysis tape did not deteriorate in the case where a low-humidity airflow was supplied to the small section in accordance with the present invention.

As described in the foregoing, in the analyzer of the present invention, in which a small section is formed in the tape-feeding cassette between the opening through which the tape is taken out of the tape-feeding cassette and the area in which the tape is accommodated in the tape-feeding cassette and in which a low-humidity airflow is supplied to that section, the whole portion of the analysis tape accommodated in the cold-storage chamber can be maintained under desirable dry conditions for a long time, and in particular, the tape can be prevented from deteriorating due to the increase in the moisture content in the analysis tape near the opening through which the tape is taken out of the cassette.

We claim:

1. A chemical analyzer used in combination with a tape-feeding cassette containing a chemical analysis tape and having means defining an opening through which said chemical analysis tape is taken out of said cassette, said analyzer comprising:

a cold-storage chamber for accommodating said tape-feeding cassette, wherein said cassette is detachable from said cold-storage chamber;

said cold-storage chamber accommodating said cassette such that said opening is positioned and arranged to lead outside of said cold-storage chamber;

said opening having a first sealing means for restricting air from entering said opening but permitting said tape to pass therethrough;

said cassette having a section located between said opening and said cold-storage chamber, said tape passing through said section, and a second sealing means for restricting air from entering into said cassette accommodated in said cold-storage chamber but permitting said tape to pass therethrough, said second sealing means being disposed between said section and other parts of said cassette; and air providing means for providing said section with air which has a relative humidity not higher than 70% such that a pressure in said section is positive.

2. An analyzer as defined in claim 1, wherein said tape is in the form of a roll.

3. An analyzer as defined in claim 1, wherein said tape-feeding cassette contains a desiccating agent which consists essentially of zeolite or silica gel.

4. An analyzer as defined in claim 1, wherein said air providing means includes means for establishing a positive pressure in said section within a range of 4 to 60 mmHg.

5. An analyzer as defined in claim 1, wherein said air providing means comprises a low-humidity generating device.

6. An analyzer as defined in claim 1, wherein said air providing means comprises a duct leading to said section.

* * * * *